United States Patent
Dekeyser et al.

[11] Patent Number: 6,083,942
[45] Date of Patent: Jul. 4, 2000

[54] PESTICIDAL HETERO-SUBSTITUTED OXADIAZINE COMPOUNDS

[75] Inventors: Mark Achiel Dekeyser, Waterloo, Canada; Paul Thomas McDonald, Middlebury, Conn.

[73] Assignees: Uniroyal Chemical Company, Inc., Middlebury, Conn.; Uniroyal Chemical Co., Elmira, Canada

[21] Appl. No.: 09/264,310

[22] Filed: Mar. 8, 1999

[51] Int. Cl.[7] .................... A01N 43/88; C07D 237/14
[52] U.S. Cl. ............................ 514/229.2; 544/66
[58] Field of Search ............... 544/66; 514/229.2

[56] References Cited

U.S. PATENT DOCUMENTS

| | | | |
|---|---|---|---|
| 3,420,825 | 1/1969 | Trepanier | 544/66 |
| 3,420,826 | 1/1969 | Trepanier | 544/66 |
| 5,536,720 | 7/1996 | Dekeyser et al. | 544/66 |
| 5,804,579 | 9/1998 | Dekeyser et al. | 544/66 |

FOREIGN PATENT DOCUMENTS

| | | |
|---|---|---|
| 11049755 | 2/1999 | Japan . |

OTHER PUBLICATIONS

Trepanier et al. 5,6–Dihydro–4H–1,3,4–oxadiazines. J. Med. Chem 9, 753–758, 1966.

*Primary Examiner*—Mukund J. Shah
*Assistant Examiner*—V Balasubramanian
*Attorney, Agent, or Firm*—Daniel Reitenbach

[57] ABSTRACT

Pesticidal substituted oxadiazines having the formula:

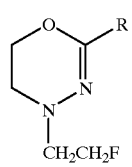

(I)

wherein R is a substituted or unsubstituted heterocyclic group, pesticidal compositions containing these oxadiazines, and methods for their use.

18 Claims, No Drawings

PESTICIDAL HETERO-SUBSTITUTED OXADIAZINE COMPOUNDS

FIELD OF THE INVENTION

This invention relates to pesticidal substituted oxadiazine compounds, pesticidal compositions containing the oxadiazine compounds, and methods for their use.

BACKGROUND OF THE INVENTION

Certain oxadiazine compounds have been described as useful as pesticides and as pharmaceutical agents. For example, U.S. Pat. No. 5,804,579 describes certain substituted oxadiazine compounds useful as insecticides. U.S. Pat. No. 5,536,720 describes substituted 2-phenyl-1,3,4-oxadiazine-4-carbamide compounds useful as insecticides and acaricides. Trepanier et al, J. Med. Chem 9: 753–758 (1966) describe certain 2-substituted 4H-1,3,4-oxadiazines useful as anticonvulsants in mice. U.S. Pat. No. 3,420,826 describes certain 2,4,6-substituted 4H-1,3,4-oxadiazines, useful as sedatives, anticonvulsants, and as pesticides against nematodes, plants, and fungi. U.S. Pat. No. 3,420,825 describes methods for producing certain 2,4,6-substituted 4H-1,3,4-oxadiazines.

It is a purpose of this invention to provide novel oxadiazine derivatives useful as pesticides.

SUMMARY OF THE INVENTION

The present invention relates to a compound having the formula:

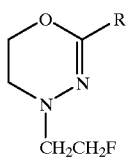

(I)

wherein R is
(a) a $C_4$–$C_5$ heterocyclic group comprising one nitrogen, sulfur, or oxygen atom, such as, e.g., pyridyl, thienyl, or furanyl;
(b) a benzo-fused $C_4$–$C_5$ heterocyclic group comprising one nitrogen, sulfur, or oxygen atom, such as, e.g., benzothienyl, benzofuranyl, or quinolinyl;
(c) a $C_3$–$C_4$ heterocyclic group comprising one nitrogen and one sulfur or oxygen atom, or two nitrogen atoms, such as, e.g., thiazoyl, oxazoyl, imidazoyl, or morpholinyl;
(d) a benzo-fused $C_3$–$C_4$ heterocyclic group comprising one nitrogen and one sulfur or oxygen atom, or two nitrogens, such as, e.g., benzthiazoyl or benzimidazoyl, wherein the heterocyclic group or the benzo-fused heterocyclic group can be unsubstituted or substituted with 1, 2, or 3 halogen atoms, $C_1$–$C_4$ haloalkyl groups, or $C_1$–$C_4$ alkyl groups.

The compounds and compositions of this invention are useful as plant protecting agents against pests such as insects, fungi, acarids, and/or nematodes.

This invention also relates to: (a) a method for controlling insects which comprises applying to a locus to be protected, an effective amount of an insecticidal compound of formula; (b) a method for controlling mites which comprises applying to a locus to be protected, an effective amount of an miticidal compound of formula I; (c) a method for controlling nematodes which comprises applying to a locus to be protected, an effective amount of an nematicidal compound of formula I; and (d) a method for controlling fungi which comprises applying to a locus to be protected, an effective amount of an fungicidal compound of formula I.

This invention further relates to a pesticidal composition comprising: (a) an effective amount of one or more compounds of formula I, and (b) a suitable carrier. More preferably, this invention relates to: (i) an insecticidal composition comprising: (a) an effective amount of one or more insecticidal compounds of formula I, and (b) a suitable carrier; (ii) a miticidal composition comprising: (a) an effective amount of one or more miticidal compounds of formula I, and (b) a suitable carrier; (iii) a nematicidal composition comprising: (a) an effective amount of one or more nematicidal compounds of formula I, and (b) a suitable carrier; and (iv) a fungicidal composition comprising: (a) an effective amount of one or more fungicidal compounds of formula I, and (b) a suitable carrier.

DETAILED DESCRIPTION OF THE INVENTION

Preferably, the compound of this invention has the formula:

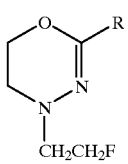

(I)

wherein R
(a) an aromatic $C_4$–$C_5$ heterocyclic group comprising one nitrogen, sulfur, or oxygen atom, such as, e.g., pyridyl, thienyl, or furanyl;
(b) a benzo-fused aromatic $C_4$–$C_5$ heterocyclic group comprising one nitrogen, sulfur, or oxygen atom, such as, e.g., benzothienyl, benzofuranyl, or quinolinyl; or
(c) an aromatic $C_3$–$C_4$ heterocyclic group comprising one nitrogen and one sulfur or oxygen atom, or two nitrogen atoms, such as, e.g., thiazoyl, oxazoyl, imidazoyl, or morpholinyl,
wherein the heterocyclic group or the benzo-fused heterocyclic group can be optionally substituted by 1 to 3 bromo or chloro atoms, more preferably, one bromo or one chloro, or by 1–3 $C_1$–$C_4$ alkyl groups, more preferably, one methyl or one ethyl.

More preferably, R is a thienyl, furanyl, pyridinyl, thiazoyl or benzothienyl group, optionally substituted by 1 to 3 bromo or chloro atoms, more preferably, one bromo or one chloro, or by 1 to 3 $C_1$–$C_4$ alkyl groups, more preferably, one methyl or one ethyl.

The compounds of this invention can be prepared by reacting a hydrazide of formula (II) below

R—CONHNH$_2$ (II)

where R has the meanings described above, with 1-bromo-2-fluoroethane in the presence of a base. Such bases include alkali metal hydroxides such potassium hydroxide, sodium hydroxide, potassium carbonate, or sodium carbonate.

The compositions of the present invention can be prepared by formulating one or more compounds of the present invention with a suitable carrier.

Suitable liquid carriers can comprise water, alcohols, ketones, phenols, toluene and xylenes. In such formulations, additives conventionally employed in the art can be utilized, such as one or more surface active agents and/or inert diluents, to facilitate handling and application of the resulting pesticidal composition.

Alternatively, the compounds of this invention can be applied as a liquid or in sprays when utilized in a liquid carrier, such as a solution comprising a compatible solvent such as acetone, benzene, toluene or kerosene, or a dispersion comprising a suitable non-solvent medium such as water.

The compositions of this invention can alternatively comprise solid carriers taking the form of dusts, granules, wettable powders, pastes, aerosols, emulsions, emulsifiable concentrates, and water-soluble solids. For example, the compounds of this invention can be applied as dusts when admixed with or absorbed onto powdered solid carriers, such as mineral silicates, talc, pyrophyllite and clays, together with a surface-active dispersing agent so that a wettable powder is obtained which then is applied directly to the loci to be treated. Alternatively, the powdered solid carrier containing the compound admixed therewith, can be dispersed in water to form a suspension for application in such form.

Granular formulations of the compounds are preferred for field treatment and are suitable for application by broadcasting, side dressing, soil incorporation or seed treatment, and are suitably prepared using a granular or pelletized form of carrier such as granular clays, vermiculite, charcoal or corn cobs. The compound of this invention is dissolved in a solvent and sprayed onto an inert mineral carrier such as attapulgite granules (10–100 mesh), and the solvent is then evaporated. Such granular compositions can contain from 2–25% of a compound of this invention, based on carrier plus compound, preferably, 3–15%. In addition, the compounds of this invention can also be incorporated into a polymeric carrier such as polyethylene, polypropylene, butadiene-styrene, styrene-acrylonitrile resins, polyamides, poly(vinyl acetates), and the like. When encapsulated, the compound of this invention can advantageously be released over an even longer time period, extending its effectiveness further than when used in non-encapsulated form.

Another method of applying the compound of this invention to the loci to be treated is by aerosol treatment, for which the compound can be dissolved in an aerosol carrier which is a liquid under pressure but which is a gas at ordinary temperature (e.g., 20° C.) and atmospheric pressure. Aerosol formulations can also be prepared by first dissolving the compound in a less volatile solvent and then admixing the resulting solution with a highly volatile liquid aerosol carrier.

For treatment of plants (such term including plant parts), the compounds of the invention preferably are applied in aqueous emulsions containing a surface-active dispersing agent which can be non-ionic, cationic or anionic. Suitable surface-active agents are well known in the art, such as those disclosed in U.S. Pat. No. 2,547,724 (columns 3 and 4). The compounds of this invention can be mixed with such surface-active dispersing agents, with or without an organic solvent, as concentrates for the subsequent addition of water, to yield aqueous suspensions of the compounds at desired concentration levels.

In addition, the compounds can be employed with carriers which themselves are pesticidally active, such as insecticides, acaricides, fungicides or bactericides.

It will be understood that the effective amount of a compound in a given formulation will vary depending, e.g., upon the specific pest to be combated, as well as upon the specific chemical composition and formulation of the compound being employed, the method of applying the compound/formulation and the locus of treatment. Generally, however, the effective amount of the compound of this invention can range from about 0.1 to about 95 percent by weight. Spray dilutions can be as low as a few parts per million, while at the opposite extreme, full strength concentrates of the compound can be usefully applied by ultra low volume techniques. When plants constitute the loci of treatment, concentration per unit area can range between about 0.01 and about 50 pounds per acre, with concentrations of between about 0.1 and about 10 pounds per acre preferably being employed for crops such as corn, tobacco, rice and the like.

To combat pests, sprays of the compounds can be applied to any suitable locus, such as to the pests directly and/or to plants upon which they feed or nest. The compositions of this invention can also be applied to the soil or other medium in which the pests are present.

The specific methods of application of the compounds and compositions of this invention, as well as the selection and concentration of these compounds, will vary depending upon such circumstances as crops to be protected, geographic area, climate, topography, plant tolerance, etc.

The following examples are provided to illustrate the present invention.

EXAMPLES

Example 1

Preparation of 4-(2-fluoroethyl)-5,6-dihydro-2-(4-pyridinyl)-4H-1,3,4-oxadiazine (Compound No. 1)

To 60 ml of ethanol in a 250 ml round-bottom flask was added 25 grams of 4-pyridinecarboxylic acid hydrazide and 58 grams of 1-bromo-2-fluoroethane, to prepare a reaction mixture. After stirring the reaction mixture at room temperature for 15 minutes, a solution of 24 grams of potassium hydroxide in 60 ml of water was added dropwise to the reaction mixture. The resulting reaction mixture was heated to reflux for 3 hours. The reaction mixture was then allowed to cool to room temperature. To the cooled reaction mixture was added 100 ml of water and 200 ml of dichloromethane, to prepare a mixture with an aqueous layer and an organic layer. The organic layer was separated and extracted to leave an oil upon evaporation of the solvent. The oil was purified by column chromatography on silica gel using dichloromethane as the eluant, to produce 12 grams of 4-(2-fluoroethyl)-5,6-dihydro-2-(4-pyridinyl)-4H-1,3,4-oxadiazine as an oil.

Compounds 2–9 in Table 1 below were prepared in the same manner using correspondingly different starting heterocarboxylic acid hydrazides.

TABLE 1

[Structure: 6-membered ring with O at top, R substituent, N-N, with CH₂CH₂F on N]

| Compound No. | R | NMR Data (ppm) in $CDCl_3$ |
|---|---|---|
| 1 | 4-$C_5H_4N$ | m(4) 3.0–3.5; m(4) 4.3–5.1; m(4) 7.2–8.2 |
| 2 | 2-Cl-5-$C_5H_3N$ | m(4) 3.0–3.5; m(4) 4.3–5.1; m(3) 7.2–8.2 |
| 3 | 3-Br-5-$C_5H_3N$ | m(4) 3.0–3.5; m(4) 4.3–5.1; m(3) 7.2–8.2 |
| 4 | 2,3-$Br_2$-5-$C_4HS$ | m(4) 3.0–3.5; m(4) 4.3–5.1; s(1) 7.5 |
| 5 | 2-Br-5-$C_4H_2S$ | m(4) 3.0–3.5; m(4) 4.3–5.1; m(2) 7.0 |
| 6 | 2-Cl-5-$C_4H_2S$ | m(4) 3.0–3.5; m(4) 4.3–5.1; m(2) 7.0 |
| 7 | 2-Br-5-$C_4H_2O$ | m(4) 3.0–3.5; m(4) 4.3–5.1; m(2) 7.1 |
| 8 | 2-$CH_3$-4-$C_3HNS$ | s(3) 2.8; m(4) 4.3–5.1; m(4) 4.3–5.1; s(1) 7.2 |
| 9 | 3-Cl-2-$C_8H_4S$ | m(4) 3.0–3.5; m(4) 4.3–5.1; m(4) 7.1–7.6 |

EXAMPLE A

Stock Solution Preparation

Examples B–D and F relate to the insecticidal, miticidal, and nematicidal use of the compounds of this invention. In all these examples, a stock solution for the compounds was prepared at 3000 ppm by dissolving 0.24 gram of each compound to be tested in 8 ml of acetone and adding 72 ml of distilled water plus 3 drops of ethoxylated sorbitan monolaurate, a wetting agent. This stock solution was used in the remaining examples demonstrating the pesticidal use of representative compounds of this invention. For each example that follows, this stock solution was used and the specificized dilutions made. All the tests discussed below, which involved treatment with compounds of this invention were always repeated with controls, in which the active compound was not provided, to permit a comparison upon which the percent control was calculated.

EXAMPLE B

Southern Corn Rootworm Test

The stock solution of 3000 ppm prepared in Example A above, was diluted to 100 ppm (test solution). For each compound, 2.5 ml of the test solution was pipetted onto a filter paper (Whatman #3) at the bottom of a 100 mm petri dish. Two corn seedlings were soaked in the 100 ppm solution for 1 hour and transferred to the petri dish containing the same test solution. After 24 hours, each dish was loaded with 5 second instar larvae of Southern Corn Rootworm (*Diabrotica undecimpunctata*). After five days, the number of live larvae was noted and the percent control, corrected by Abbott's formula [see J. Economic Entomology 18: 265–267 (1925)] was calculated.

The results of the testing of Southern Corn Rootworm (CR) are presented in Table 2 below.

EXAMPLE C

Rice Planthopper Foliar Test

The stock solution of 3000 ppm prepared in Example A above, was diluted to 1000 ppm. One pot containing approximately 20 Mars variety rice seedlings was treated with each formulation by spraying with a spray atomizer. One day after treatment plants were covered with a tubular cage and twenty adult rice delphacids (*Sogatodes orizicola*), were transferred into each cage. Five days after transferring, counts were made of the surviving planthoppers in each pot and percent control was estimated.

Results of the testing of rice planthoppers (RPH) are presented in Table 2 below.

EXAMPLE D

Tobacco Budworm Test

For each compound, 0.2 ml of the stock solution prepared in Example A above, was pipetted onto the surface of each of 5 diet cells, allowed to spread over the surfaces and air dried for two hours. Then a second instar of tobacco budworm (*Helicoverpa virescens*) larva was introduced into each cell. After 14 days, the number of living larvae was determined for each treatment and percent control, corrected by Abbott's formula, was calculated.

The results of the testing of tobacco budworms (TB) are presented in Table 2 below.

EXAMPLE E

Tobacco Budworm Ovicide Test

A solution of 1000 ppm was prepared by dissolving 0.015 g of the compound to be tested in 2 ml of acetone and adding 13 ml of distilled water plus 1 drop of ethoxylated sorbitan monolaurate. Cheesecloth on which budworms had oviposited eggs 1–2 days before treatment was cut into pieces, each containing 40–80 eggs. Each piece was immersed for 1 minute in the test solution, then placed on moist filter paper and enclosed in a petri dish until evaluation. After 5 days, the numbers of hatched and unhatched eggs were counted and an adjusted percent control determined. The results of the testing of tobacco budworm ovicide (TBOV) are given in Table 2 below.

EXAMPLE F

Mite Adulticide and Mite Ovicide Tests

One day before treatment of cowpea primary leaves with the test solutions, a "Figure 8" configuration of tree tanglefoot was applied to each of two cowpea primary leaves, one from each of two plants in a pot. In each figure, the circle nearer the stem was designated for the mite ovicide test and the circle further from the stem was designated for the mite adulticide test.

Groups of adult mites (*Tetranychus urticae* Koch) were transferred into ovicide circles one day before treatment and the females were allowed to deposit eggs until one hour before treatment, at which point all the adults were removed. The plants were then sprayed to run off with a 1000 ppm solution diluted from the 3000 ppm stock solution.

One day following treatment of the plants with the test solution, groups of approximately 25 adult mites were transferred into the adulticide rings. Five days later these rings were examined for live mites remaining on the leaves. The percent control was estimated based on the number of mites surviving on the control plants.

Nine days following treatment the ovicide rings were examined for unhatched eggs and living immature mites. The percent control was estimated based on the number of unhatched eggs.

Results of the mite adulticide (MI) and ovicide (MIOV) tests are presented below in Table 2.

EXAMPLE G
Nematode Test

The stock solution (3000 ppm) was diluted to 1000 ppm (test solution). For each test solution, 25 ml was drenched onto separate 500 grams of soil infested with root knot nematode (*Meloidogyne incognita*) eggs in a pot, for a soil concentration of 50 ppm sc.

One day after treatment, two tomato seedlings were planted in each pot. Nineteen days after planting, the roots were evaluated for the presence of knots or galls, and the percent control was estimated based on the infestation levels in check plants.

The results of the testing of nematodes (NE) are given in Table 2 below.

TABLE 2

| Cmpd. No. | Pesticidal Activity Percent Control | | | | | | |
|---|---|---|---|---|---|---|---|
| | CR | MI | MIOV | RPH | TB | TBOV | NE |
| 1 | 0 | 0 | 100 | 0 | 20 | 95 | 0 |
| 2 | 100 | 0 | 100 | 80 | 100 | 100 | PT |
| 3 | 0 | 0 | 100 | 85 | 60 | 100 | 0 |
| 4 | 0 | 0 | 30 | 0 | 100 | 100 | PT |
| 5 | 40 | 0 | 100 | 0 | 100 | 100 | 70 |
| 6 | 100 | 0 | 100 | 0 | 100 | 100 | 0 |
| 7 | 100 | 0 | 100 | 0 | 60 | 100 | 0 |
| 8 | 0 | 70 | 100 | 90 | 0 | NT | PT |
| 9 | 40 | 0 | 100 | 85 | 100 | 99 | 70 |

PT = Phytotoxic
NT = Not tested

EXAMPLE H
Control of Nine Fungal Species

Compounds 1, 2, 3, 5, 6, 7, and 9 from Table 1 were each solubilized in acetone at a concentration of 500 mg/ml. Each solution was prepared so that there was 500 parts by weight of active compound per million parts by volume of acetone. Separate filter paper discs (11 cm diameter) were dipped in each of the test solutions. The discs were then allowed to air dry to evaporate the acetone solvent. Untreated discs (i.e., undipped) were used as controls.

The treated and untreated discs were then placed on nutrient agar plates and inoculum plugs of each tested fungi were added to the center of separate treated and untreated discs with the fungus mat of the plug in direct contact with the paper of the disc. For *Cercosporidium personatum*, 2 drops of spore suspension (20,000 spores/ml) were added to the discs rather than an inoculum plug. The agar plates with the discs were incubated at 29° C. for 3–7 days according to the growth rate of the individual fungi. At the optimum time of untreated control growth for each fungus, radial measurements (mm) of colony growth were made for both the treated and untreated discs for such fungus.

Percent growth inhibition of each the tested compounds was determined as a function of the difference between the colony radii of the treated and untreated disc for the fungus species except for *Cercosporidium personatum*. For the *Cercosporidium personatum*, the degree of spore germination was graded on a color scale of 0 (colorless) for complete inhibition to 10 for black (maximum germination of untreated species). These scores were then compared with the scores of the untreated discs for percent inhibition (or percent control).

The fungus species tested were:
*Rizoctonia solari*
*Pythium ultimum*
*Fusarium oxysporum*
*Collectotrichum gossypii*
*Phytopthora infestans*
*Botrylis cinera*
*Cercosporidium personatum*
*Septoria nodorum*
*Sclerotinia minor*

The results are shown in Table 3 below.

TABLE 3

| | Fungicidal Activity Percent Control (Inhibition) (500 ppm) | | | | | | |
|---|---|---|---|---|---|---|---|
| | Compound No. | | | | | | |
| Fungus Species | 1 | 2 | 3 | 5 | 6 | 7 | 9 |
| *Rhizoctonia solari* | 0 | 10 | 80 | 100 | 80 | 97 | 93 |
| *Pythium ultimum* | 5 | 5 | 25 | 100 | 70 | 70 | 91 |
| *Fusarium oxysporum* | 100 | 20 | 100 | 55 | 60 | 100 | 83 |
| *Colletotrichum gossypii* | 5 | — | 70 | 0 | 40 | 100 | 85 |
| *Phytophthora infestans* | — | — | — | 76 | — | — | 75 |
| *Botrytis cinerea* | 45 | — | 100 | 93 | 70 | 0 | 90 |
| *Cercosporidium personatum* | — | — | 35 | 90 | 30 | 50 | 98 |
| *Septoria nodorum* | 96 | 70 | 100 | 95 | 80 | 85 | 90 |
| *Sclerotinia minor* | 93 | 5 | 100 | — | 89 | 87 | 93 |

What is claimed is:

1. A compound having the formula:

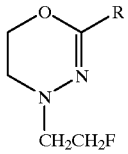

(I)

wherein R is
   (a) a $C_4$–$C_5$ heterocyclic group having one nitrogen, sulfur, or oxygen atom;
   (b) a benzo-fused $C_4$–$C_5$ heterocyclic group having one nitrogen, sulfur, or oxygen atom;
   (c) a $C_3$–$C_4$ heterocyclic group having one nitrogen and one sulfur or oxygen atom, or two nitrogen atoms; or
   (d) a benzo-fused $C_3$–$C_4$ heterocyclic group having one nitrogen and one sulfur or oxygen atom, or two nitrogens,
wherein the heterocyclic group or the benzo-fused heterocyclic group can be unsubstituted or substituted with 1, 2, or 3 halogen atoms, $C_1$–$C_4$ haloalkyl groups, or $C_1$–$C_4$ alkyl groups.

2. A compound as recited in claim 1 wherein the heterocyclic group or benzo-fused heterocyclic group is aromatic.

3. A compound as recited in claim 2 wherein R is
   (a) an aromatic $C_4$–$C_5$ heterocyclic group having one nitrogen, sulfur, or oxygen atom;
   (b) a benzo-fused aromatic $C_4$–$C_5$ heterocyclic group having one nitrogen, sulfur, or oxygen atom; or
   (c) an aromatic $C_3$–$C_4$ heterocyclic group having one nitrogen and one sulfur or oxygen atom, or two nitrogen atoms,
wherein the heterocyclic group or the benzo-fused heterocyclic group can be optionally substituted by 1 to 3 bromo or chloro atoms or by 1–3 $C_1$–$C_4$ alkyl groups.

4. A compound as recited in claim 3 wherein the heterocyclic group or the benzo-fused heterocyclic group is unsubstituted or substituted by one bromo or one chloro, or by one methyl or one ethyl.

5. A compound as recited in claim 4 wherein the heterocyclic group or the benzo-fused heterocyclic group is selected from the group consisting of pyridyl, thienyl, furanyl, benzothienyl, benzofuranyl, quinolinyl, thiazoyl, oxazoyl, imidazoyl, and morpholinyl.

6. A compound as recited in claim 5 wherein the heterocyclic group or the benzo-fused heterocyclic group is selected from the group consisting of pyridyl, thienyl, furanyl, benzothienyl, and thiazoyl.

7. A composition comprising an insecticidally, miticidally, fungicidally, or nematocidally effective amount of a compound as recited in claim 1 and a suitable carrier.

8. A method for controlling insects which comprises applying to a locus to be protected, an effective amount of an insecticidal compound as recited in claim 1.

9. A method for controlling insects which comprises applying to a locus to be protected, an effective amount of an insecticidal compound as recited in claim 3.

10. A method for controlling mites which comprises applying to a locus to be protected, an effective amount of a miticidal compound as recited in claim 1.

11. A method for controlling mites which comprises applying to a locus to be protected, an effective amount of a miticidal compound as recited in claim 3.

12. A method for controlling fungi on plants, on seeds, or in the soil, which method comprises applying to a locus to be protected, an effective amount of a fungicidal compound as recited in claim 1.

13. A method for controlling fungi on plants, on seeds, or in the soil, which method comprises applying to a locus to be protected, an effective amount of a fungicidal compound as recited in claim 3.

14. A method for controlling nematodes which comprises applying to a locus to be protected, an effective amount of a nematicidal compound as recited in claim 1.

15. A method for controlling nematodes which comprises applying to a locus to be protected, an effective amount of a nematicidal compound as recited in claim 3.

16. A compound having the formula:

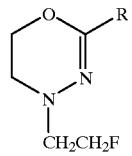

(I)

wherein R is (a) a $C_4$–$C_5$ heterocyclic group having one sulfur atom;

(b) a benzo-fused $C_4$–$C_5$ heterocyclic group having one sulfur atom;

(c) a $C_3$–$C_4$ heterocyclic group having one nitrogen and one sulfur; or (d) a benzo-fused $C_3$–$C_4$ heterocyclic group having one nitrogen and one sulfur atom, wherein the heterocyclic group or the benzo-fused heterocyclic group can be unsubstituted or substituted with 1, 2, or 3 halogen atoms, $C_1$–$C_4$ haloalkyl groups, or $C_1$–$C_4$ alkyl groups.

17. A compound as recited in claim 16 wherein R is (a) an aromatic $C_4$–$C_5$ heterocyclic group having one sulfur atom;

(b) a benzo-fused aromatic $C_4$–$C_5$ heterocyclic group having one sulfur atom; or (c) an aromatic $C_3$–$C_4$ heterocyclic group having one nitrogen and one sulfur atom, wherein the heterocyclic group or the benzo-fused heterocyclic group can be optionally substituted by 1 to 3 bromo or chloro atoms or by 1–3 $C_1$–$C_4$ alkyl groups.

18. A compound as recited in claim 17 wherein the heterocyclic group or the benzo-fused heterocyclic group is selected from the group consisting of thienyl, benzothienyl, and thiazoyl.

* * * * *